(12) United States Patent
Ghosh et al.

(10) Patent No.: US 10,710,058 B2
(45) Date of Patent: Jul. 14, 2020

(54) PROCESS FOR PREPARING HYDROCRACKING CATALYST

(71) Applicant: SABIC GLOBAL TECHNOLOGIES B.V., Bergen op Zoom (NL)

(72) Inventors: Ashim Kumar Ghosh, Houston, TX (US); Alla Khanmamedova, Sugar Land, TX (US)

(73) Assignee: SABIC GLOBAL TECHNOLOGIES B.V., Bergen op Zoom (NL)

(*) Notice: Subject to any disclaimer, the term of this patent is extended or adjusted under 35 U.S.C. 154(b) by 0 days.

(21) Appl. No.: 16/317,387

(22) PCT Filed: Aug. 1, 2017

(86) PCT No.: PCT/IB2017/054705
§ 371 (c)(1),
(2) Date: Jan. 11, 2019

(87) PCT Pub. No.: WO2018/025183
PCT Pub. Date: Feb. 8, 2018

(65) Prior Publication Data
US 2019/0321809 A1 Oct. 24, 2019

(30) Foreign Application Priority Data
Aug. 2, 2016 (EP) ..................... 16182324

(51) Int. Cl.
| | | |
|---|---|---|
| B01J 29/06 | (2006.01) |
| B01J 29/44 | (2006.01) |
| B01J 35/00 | (2006.01) |
| B01J 35/02 | (2006.01) |
| B01J 37/00 | (2006.01) |
| B01J 37/04 | (2006.01) |
| B01J 37/08 | (2006.01) |
| C10G 7/00 | (2006.01) |
| C10G 47/18 | (2006.01) |
| B01J 29/068 | (2006.01) |
| B01J 29/12 | (2006.01) |
| B01J 29/22 | (2006.01) |
| B01J 29/74 | (2006.01) |
| B01J 29/67 | (2006.01) |

(52) U.S. Cl.
CPC ............ B01J 29/44 (2013.01); B01J 29/068 (2013.01); B01J 29/123 (2013.01); B01J 29/126 (2013.01); B01J 29/22 (2013.01); B01J 29/67 (2013.01); B01J 29/74 (2013.01); B01J 35/002 (2013.01); B01J 35/006 (2013.01); B01J 35/0013 (2013.01); B01J 35/026 (2013.01); B01J 37/0009 (2013.01); B01J 37/04 (2013.01); B01J 37/08 (2013.01); C10G 7/00 (2013.01); C10G 47/18 (2013.01); *B01J 2229/186* (2013.01); *B01J 2229/20* (2013.01); *B01J 2229/42* (2013.01); *C07C 2529/06* (2013.01); *C07C 2529/068* (2013.01); *C07C 2529/08* (2013.01); *C07C 2529/12* (2013.01); *C07C 2529/18* (2013.01); *C07C 2529/22* (2013.01); *C07C 2529/40* (2013.01); *C07C 2529/44* (2013.01); *C07C 2529/65* (2013.01); *C07C 2529/67* (2013.01); *C07C 2529/70* (2013.01); *C10G 2300/1044* (2013.01); *C10G 2300/4006* (2013.01); *C10G 2300/4018* (2013.01); *C10G 2300/70* (2013.01); *C10G 2400/30* (2013.01)

(58) Field of Classification Search
CPC ...... B01J 29/068; B01J 29/123; B01J 29/126; B01J 29/22; B01J 29/44; B01J 29/67; B01J 29/74; B01J 2229/20; B01J 2229/186; B01J 2229/42; B01J 35/006; B01J 35/0013; B01J 35/002; B01J 35/026; B01J 37/04; B01J 37/08; B01J 37/0009; C10G 2300/70; C07C 2529/06; C07C 2529/068; C07C 2529/08; C07C 2529/12; C07C 2529/18; C07C 2529/22; C07C 2529/40; C07C 2529/44; C07C 2529/70; C07C 2529/74; C07C 2529/65; C07C 2529/67
USPC ........ 502/60, 63, 64, 66, 68, 69, 71, 74, 77, 502/78, 79
See application file for complete search history.

(56) References Cited

U.S. PATENT DOCUMENTS

| | | |
|---|---|---|
| 5,865,986 A | 2/1999 | Buchanan et al. |
| 9,314,779 B2 | 4/2016 | Ghosh et al. |
| 2002/0092797 A1 | 7/2002 | Choi et al. |
| 2009/0118556 A1* | 5/2009 | Euzen ............... B01J 21/12 585/251 |

(Continued)

FOREIGN PATENT DOCUMENTS

WO        2007055488 A1        5/2007

OTHER PUBLICATIONS

International Search Report; International Application No. PCT/EP2010/066961; International Filing Date: Aug. 1, 2017; dated Oct. 27, 2017; 6 pages.

(Continued)

*Primary Examiner* — Elizabeth D Wood
(74) *Attorney, Agent, or Firm* — Cantor Colburn LLP

(57) ABSTRACT

Disclosed herein is a process for preparing a hydrocracking catalyst, comprising (i) combining a zeolite, a binder, water and a hydrogenating metal compound which is a complex or a salt of a hydrogenating metal to obtain a mixture, wherein the zeolite has not been treated with a phosphorus-containing compound and the zeolite has a silica to alumina molar ratio of 5-200; (ii) forming the mixture into a shaped body; and (iii) calcining the shaped body to form the catalyst.

20 Claims, 1 Drawing Sheet

(56) References Cited

U.S. PATENT DOCUMENTS

| | | |
|---|---|---|
| 2012/0083638 A1 | 4/2012 | Boldingh et al. |
| 2014/0046109 A1* | 2/2014 | Ghosh ..................... B01J 37/04 |
| | | 585/466 |
| 2014/0058157 A1* | 2/2014 | Negiz ....................... C07C 2/66 |
| | | 585/467 |
| 2014/0377140 A1* | 12/2014 | Zimmerman .......... B01D 3/009 |
| | | 422/187 |
| 2015/0126791 A1 | 5/2015 | Kijlstra et al. |

OTHER PUBLICATIONS

Written Opinion; International Application No. PCT/EP2010/066961; International Filing Date: Aug. 1, 2017; dated Oct. 27, 2017; 6 pages.

\* cited by examiner

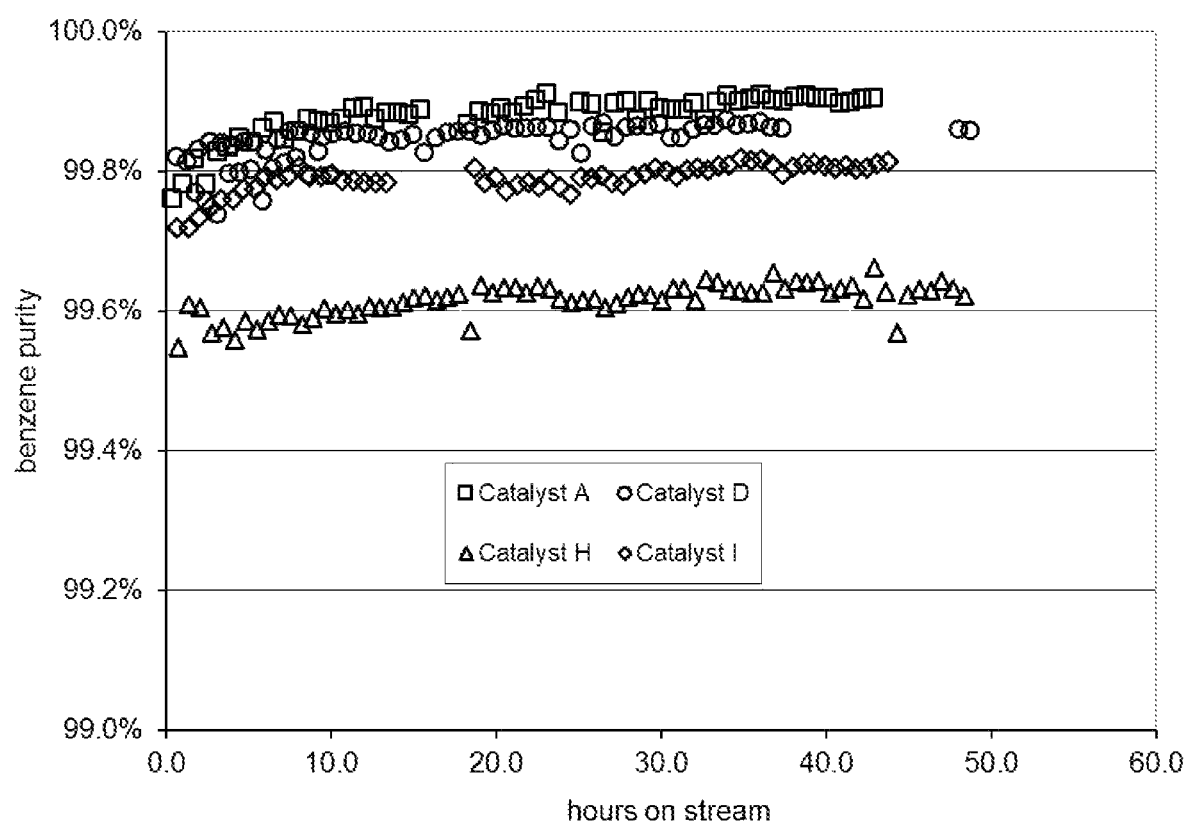

PROCESS FOR PREPARING HYDROCRACKING CATALYST

CROSS REFERENCE TO RELATED APPLICATIONS

This application is a 371 of International Application No. PCT/IB2017/054705, filed Aug. 1, 2017, which is incorporated herein by reference and which claims priority to European Application No. 16182324.0 filed Aug. 2, 2016.

The present invention relates to a process for preparing a hydrocracking catalyst and the catalyst obtainable thereby. The present invention also relates to a process for hydrocracking a feed stream comprising hydrocarbons using the catalyst.

A hydrocracking catalyst comprising a hydrogenation metal, a zeolite and a binder is well-known. For example, WO2008015027 describes a process for the catalytic hydrodealkylation of hydrocarbon compositions by treating said hydrocarbon compositions with a catalyst in the presence of hydrogen. The catalyst consists of a ZSM-5 zeolite, has a Si/Al molar ratio within the range of 5 to 100, and is modified by means of the metals platinum and molybdenum. In the examples of WO2008015027, the catalyst is obtained by mixing a ZSM-5 zeolite and an alumina as a binder, extruding the mixture, calcining the extruded product and crushing and sieving to produce a catalyst powder. This catalyst powder is impregnated with an aqueous solution of ammonium molybdate followed by an impregnation with an aqueous solution of platinum tetraamine nitrate and a subsequent calcination. WO2013/182534 discloses a process for producing BTX from a $C_5$-$C_{12}$ hydrocarbon mixture using a hydrocracking/hydrodesulphurisation catalyst. According to WO2013/182534, the process results in a mixture comprising substantially no co-boilers of BTX, thus chemical grade BTX can easily be obtained. The catalyst used in WO2013/182534 comprises 0.1-1 wt % hydrogenation metal in relation to the total catalyst weight and a zeolite having a silica ($SiO_2$) to alumina ($Al_2O_3$) molar ratio of 5-200. In the examples, zeolite was mixed with an alumina binder to provide bound zeolite particles. The bound zeolite particles were mixed with platinum-modified gamma-alumina particles to provide a catalyst composition.

WO2007/006473 discloses a process for improving the properties as a fuel of hydrotreated hydrocarbon blends which comprises putting said hydrotreated blends in contact with hydrogen, in the presence of a catalytic system, comprising: a) one or more metals selected from Pt, Pd, Ir, Ru, Rh and Re and b) a silico-aluminate of an acidic nature such a zeolite. The component b) can be in the form of an extruded product with traditional ligands, such as aluminum oxide, boehmite or pseudoboehmite.

WO2007/055488 discloses is a process of preparing aromatic hydrocarbons and liquefied petroleum gas from a hydrocarbon mixture. A non-aromatic compound in the hydrocarbon feedstock mixture is converted into a gaseous material through hydrocracking, and an aromatic compound therein is converted into an oil component through dealkylation and transalkylation.

US 2012/083638 discloses a process for aromatic transalkylation and olefin reduction of a feed stream. Transalkylation conditions produce xylenes and reduced olefins in the feed. The process may be used in a xylene production facility to minimize or avoid the necessity of feedstock pretreatment such as hydrotreating, hydrogenation, or treating with clay and/or molecular sieves.

US 2015/126791 is directed to a process for the preparation of a naphtha-selective hydrocracking catalyst comprising of from 3 to 4.8% wt of molybdenum, calculated as metal, and from 1.5 to 3% wt of nickel, calculated as metal, which comprises loading a refractory oxide support comprising an alumina binder component and a zeolite Y component in a content of from 65 to 75 wt % based on the total weight of the catalyst, with nickel and molybdenum in the presence of citric acid.

U.S. Pat. No. 5,865,986 is directed to a process for upgrading a petroleum naphtha fraction. The naphtha is subjected to reforming and the reformate is cascaded to a benzene and toluene synthesis zone over a benzene and toluene synthesis catalyst comprising steamed ZSM-5. In one aspect, the benzene and toluene synthesis catalyst includes a metal hydrogenation component such as cobalt, nickel, platinum or palladium. In one mode of operation, the benzene and toluene synthesis catalyst replaces at least a portion of the catalyst of the reformer.

US 2002/092797 discloses a process for producing aromatic hydrocarbon compounds and liquefied petroleum gas and a catalyst useful therefor. In the presence of said catalyst, aromatic components in the hydrocarbon feedstock are converted to BTX-enriched components of liquid phase through hydrodealkylation and/or transalkylation, and non-aromatic components are converted to LPG-enriched gaseous materials through hydrocracking.

It is an objective of the invention to provide an improved process for the preparation of a catalyst.

Accordingly, the present invention provides a process for preparing a hydrocracking catalyst, comprising (i) combining a zeolite, a binder, water and a hydrogenating metal compound which is a complex or a salt of a hydrogenating metal to obtain a mixture, e.g., a paste such as an extrudable paste, wherein the zeolite has not been treated with a phosphorus-containing compound and the zeolite has a silica ($SiO_2$) to alumina ($Al_2O_3$) molar ratio of 5-200;

(ii) forming the mixture into a shaped body; and (iii) calcining the shaped body to form the catalyst.

BRIEF DESCRIPTION OF THE SEVERAL VIEWS OF THE DRAWING

FIG. 1 illustrates catalyst activity.

According to the process of the invention, the hydrogenating metal compound is added to the zeolite or binder or their mixture before a shaped body is formed. It was found that a catalyst prepared by depositing the hydrogenating metal on an extrudate comprising a zeolite and a binder can have an uneven distribution of the hydrogenating metal between the outer surface and the inner body of the extrudate. This leads to variation in the catalyst performance. In this prior art method, specific measures are necessary to prevent this variation in the catalyst performance, such as the addition of a specific additive. According to the process of the invention, uneven distribution of the hydrogenating metal was prevented in a simple manner.

It is noted that U.S. Pat. No. 9,314,779 discloses a method of forming a catalyst by treating a detemplated ZSM-5 zeolite material with a phosphorus-containing compound to form a phosphorus treated zeolite before combining it with a hydrogenating material and a binder material to form a mixture. The phosphorus content of the prepared catalyst is typically 1 to 15 weight % based on the total weight of zeolite. The prepared catalyst of U.S. Pat. No. 9,314,779 is a catalyst for aromatic alkylation. The hydrocracking catalyst according to the present invention is prepared without a prior treatment of the zeolite by a phosphorus-containing compound. This can also be verified by the amount of phosphorus in the zeolite. For example, if the zeolite used in step (i) contains less than 0.01 wt % of phosphorus with respect to the zeolite, it is understood that the zeolite has not been treated with phosphorus compounds. The process according to the present invention also does not involve treatment of the mixture of step (i) or the shaped body of step (ii) by a phosphorus-containing compound.

Step (i)

The method comprises (i) combining a zeolite, a binder, a hydrogenating metal compound and water to obtain a mixture. The mixture can be mixed, e.g., for a period of time of less than 30 minutes, or less than or equal to 20 minutes, preferably less than or equal to 10 minutes. In other words, the mixture is mixed to be more homogenous.

Preferably, the hydrogenating metal compound is provided as an aqueous solution. However, it is also possible that hydrogenating metal compound is provided as a solid. In this case, the water is provided separately from the solid.

The water in step (i) may be provided as a component of an aqueous solution comprising the hydrogenating metal compound. However, water is preferably added in addition to the aqueous solution. Desirably, the amount of water is only enough to form a paste, e.g., an extrudable paste. An extrudable paste is a paste that is capable of being formed into a shaped body through extrusion. Desirably, the water is added by spraying.

In some embodiments, step (i) involves combining the zeolite and the hydrogenating metal compound and subsequently adding the binder to the combination of the zeolite and the hydrogenating metal compound. The hydrogenating metal compound to be combined with the zeolite may be provided in the form of an aqueous solution. Preferably, (additional) water is added to the combination of the zeolite, the hydrogenating metal compound and the binder. For example, an aqueous solution of the hydrogenating metal compound is added to the zeolite and mixed, and subsequently the binder is mixed with the mixture of the zeolite and the aqueous solution of the hydrogenating metal compound, and finally water is added to obtain a mixture which can be shaped into a desired shape.

In some embodiments, step (i) involves combining the hydrogenating metal compound and the binder and subsequently adding the zeolite to the combination of the binder and the hydrogenating metal compound. The hydrogenating metal compound to be combined with the binder may be provided in the form of an aqueous solution. Preferably, (additional) water is added to the combination of the zeolite, the hydrogenating metal compound and the binder. For example, an aqueous solution of the hydrogenating metal compound is added to the binder and mixed, and subsequently the zeolite is mixed with the mixture of the binder and the aqueous solution of the hydrogenating metal compound, and finally water is added to obtain a mixture which can be shaped into a desired shape.

In some embodiments, step (i) involves combining the zeolite and the binder and subsequently adding the hydrogenating metal compound to the combination of the zeolite and the binder. Preferably, water is added to the combination of the zeolite and the binder before the hydrogenating metal compound is added. For example, the zeolite and the binder are mixed, and subsequently water is added to the mixture of the zeolite and the binder, and finally an aqueous solution of the hydrogenating metal compound is added to the moist mixture of the zeolite and the binder to obtain a mixture which can be shaped into a desired shape.

Zeolite

Zeolites are well-known molecular sieves having three dimensional structures with well-defined channels, pores, cavities with defined pore size. As used herein, the term "zeolite" or "aluminosilicate zeolite" relates to an aluminosilicate molecular sieve. An overview of their characteristics is for example provided by the chapter on Molecular Sieves in Kirk-Othmer Encyclopedia of Chemical Technology, Volume 16, p 811-853; in Atlas of Zeolite Framework Types, 5th edition, (Elsevier, 2001).

Preferably, the hydrocracking catalyst comprises a medium pore aluminosilicate zeolite or a large pore aluminosilicate zeolite or their combinations. Suitable zeolites include, but are not limited to, ZSM-5, MCM-22, ZSM-11, beta zeolite, EU-1 zeolite, faujasite (zeolite Y), ferrierite and mordenite. The term "medium pore zeolite" is commonly used in the field of zeolite catalysts.

Accordingly, a medium pore zeolite such as ZSM-5 zeolite is a zeolite having a pore size of about 5-6 angstroms (Å). Suitable medium pore size zeolites are 10-ring zeolites, i.e. the pore is formed by a ring consisting of 10 tetrahedra of $[SiO_4]$ and $[AlO_4]^-$. The negative charge arising from $[AlO_4]^-$ is neutralized by a cation in the zeolite. Suitable large pore zeolites have a pore size of about 6-8 Å and are of the 12-ring structure type. Zeolites of the 8-ring structure type are called small pore size zeolites. In the above cited Atlas of Zeolite Framework Types various zeolites are listed based on ring structure. Most preferably the zeolite is ZSM-5 zeolite, which is a well-known zeolite having MFI structure.

Preferably, the silica ($SiO_2$) to alumina ($Al_2O_3$) molar ratio of the (ZSM-5) zeolite is in the range of 20-200, more preferably in the range of 20-100, more preferably 25-75.

Using a zeolite having a $SiO_2$ to $Al_2O_3$ molar ratio of 25-75 shows the optimum catalyst hydrocracking performance to obtain desired benzene purity from a feedstock containing BTX, C9+ aromatics and nonaromatics which are mainly $C_{5-7}$ hydrocarbons. The hydrocracking activity is measured by the level of cracking of the nonaromatics to obtain desired benzene purity, wherein benzene purity is defined as benzene/(benzene plus $C_{5-7}$ non-aromatics hydrocarbons) in the product stream. In examples of the present disclosure, hydrocarbon components in product stream were measured as C %. The term "C %" is herein understood as the amount of carbon of a component divided by the total amount of carbon for sum of all components in the stream, then multiplied by 100. Means and methods for quantifying the $SiO_2$ to $Al_2O_3$ molar ratio of a zeolite are well known in the art and include, but are not limited to AAS (Atomic Absorption Spectrometer), ICP (Inductively Coupled Plasma Spectrometry) analysis or XRF (X-ray fluorescence) . It is noted that the $SiO_2$ to $Al_2O_3$ molar ratio referred herein is meant as the ratio in the zeolite prior to being mixed with the other components. Preferably, the $SiO_2$ to $Al_2O_3$ molar ratio is measured by XRF.

Preferably, the silica to alumina ratio of the ZSM-5 zeolite is in the range of 30-65, more preferably 35-60, more preferably in the range of 40-55. At such ratio, in particular when the silica to alumina ratio is at least 35, the best balance of total aromatics and methane content in the hydrocracking product stream and achievable WHSV for a desired benzene purity is obtained.

Preferably, the zeolite is in a hydrogen form or a $NH_4^-$ form, i.e. having at least a portion of the original cations associated therewith replaced by $H^+$ ions or $NH_4^+$ ions, respectively. A first method involves direct treatment employing an acid, for example a mineral acid (HNO$_3$, HCl, etc.). A second method involves direct exchange using an ammonium salt (e.g. NH$_4$NO$_3$) followed by calcination. It can optionally contain up to trace levels of other cations such as Na (wherein a trace level is at most 0.05 wt % based upon the total weight of the zeolite).

Binder

The binder material can be an inorganic oxide material. The binder material can comprise an aluminum- or silicon-containing material such as silica, alumina, clay, aluminum phosphate, silica-alumina, or combinations comprising at least one of the foregoing. Alumina (Al$_2$O$_3$) is a preferred binder. The catalyst can comprise up to 99 wt %, e.g., 1 to 99 wt %, for example 10 to 90 wt %, 10 to 50 wt % or 20 to 40 wt % of the binder based on the total weight of the catalyst.

Preferably, the binder has been treated with a mineral acid such as nitric acid, hydrochloric acid, phosphoric acid or sulfuric acid, preferably nitric acid. Treating the binder with a mineral acid improves physical strength of the formed catalyst.

Hydrogenating Metal Compound

The hydrogenating metal compound is a complex or a salt of a hydrogenating metal.

Preferably, the hydrogenating metal is at least one element selected from Group 10 of the periodic table of elements or rhodium or iridium. The preferred Group 10 elements are palladium and platinum, particularly platinum.

Preferably, the hydrogenating metal compound is a metal amine complex. Preferably, the hydrogenating metal compound is selected from the group consisting of a nitrate, a hydroxide hydrate and a chloride. Preferably, the hydrogenating metal compound is selected from the group consisting of H$_2$PtCl$_6$, (NH$_3$)$_4$Pt(NO$_3$)$_2$, (NH$_3$)$_4$Pt(OH)$_2$ and (NH$_3$)$_4$PtCl$_2$.

Step (ii)

Examples of the shaped bodies include, but are not limited to, spherically or cylindrically shaped pellets, tablets, particles and extrudates. The shaped body typically has an average diameter of about 0.1 mm to about 7 mm, typically 1.4 mm to 3.5 mm. The diameter is usually measured by slide caliper. The shaped body typically has an average length of 3 to 8 mm. The average as used herein is an arithmetic average. One specific example of the shaped body is a cylindrically shaped extrudate with an average diameter of about 1.6 mm (1/16 inch) with an average length of extrudates about 3 to 8 mm.

Step (iii)

The shaped body obtained by step (ii) is calcined, for example 250-300° C. for 2-8 hours. Calcination can be at a temperature of 250 to 295° C., e.g., 260 to 290° C. or 270 to 290° C.

Obtained Catalyst

Preferably, the catalyst according to the process of the present invention comprises 0.010-0.30 wt %, more preferably 0.010-0.15 wt %, of hydrogenating metal. In the context of the present invention, the term "wt %" when relating to the metal content as comprised in a catalyst relates to the wt % of said metal in relation to the total weight of the catalyst. The amount of the hydrogenating metal in the catalyst can be determined e.g. by subjecting the catalyst to XRF or ICP.

Even more preferably, the catalyst comprises 0.015-0.095 wt %, 0.020-0.090 wt %, 0.035-0.080 or 0.040-0.075 wt % of hydrogenating metal in relation to the total weight of the catalyst.

The catalyst can have average particle sizes of the hydrogenating metal of less than or equal to 5 nanometers (nm), for example, less than or equal to 3 nm, or less than or equal to 1 nanometers (nm). As used herein, the average particle size is determined using a High Angular Annular Dark Field (HAADF) detector in the Scanning Transmission Electron Microscopy (STEM) mode using a TECNAI-F20 microscope, measuring at least 6 particles. The hydrocracking catalyst used in the process of the invention should have a sufficient hydrogenation activity. Accordingly, it is preferred that the catalyst does not comprise secondary metals, such as tin, lead or bismuth that inhibit the hydrogenation activity of the hydrogenating metal. Preferably, the hydrocracking catalyst used in the process of the present invention accordingly comprises less than 0.01 parts tin and less than 0.02 parts lead and less than 0.01 parts bismuth (on the basis of 100 parts by weight of the total catalyst), preferably less than 0.005 parts tin and less than 0.01 parts lead and less than 0.005 parts bismuth (on the basis of 100 parts by weight of total catalyst).

Further, preferably, the hydrocracking catalyst used in the process of the present invention accordingly comprises less than 0.01 parts molybdenum (on the basis of 100 parts by weight of the total catalyst).

The invention also relates to the catalyst obtained by or obtainable by the process according to the invention.

The invention further relates to a process for hydrocracking a feed stream comprising hydrocarbons by contacting the feed stream in the presence of hydrogen with the catalyst according to the invention. The process is preferably a process for obtaining BTX. Light hydrocarbons, preferably LPG, are also obtained.

The invention further relates to a process for hydrocracking a feed stream comprising hydrocarbons, comprising the process for preparing a hydrocracking catalyst according to the invention and contacting the feed stream in the presence of hydrogen with the hydrocracking catalyst.

Preferably, the process for hydrocracking a feed stream comprising hydrocarbons according to the invention comprises (a) contacting a hydrocracking feed stream in the presence of hydrogen with the hydrocracking catalyst under process conditions including a temperature of 400-580° C. (preferably 425-580° C.), a pressure of 300-5000 kiloPascals (kPa) gauge and a Weight Hourly Space Velocity of 0.1-30 hr$^{-1}$ to produce a hydrocracking product stream comprising BTX, wherein the hydrocracking feed stream comprises C$_5$-C$_{12}$ hydrocarbons, and (b) separating the BTX from the hydrocracking product stream.

As used herein, the term "C$_n$ hydrocarbons", wherein "n" is a positive integer, is meant to describe all hydrocarbons having n carbon atoms. Moreover, the term "C$_{n+}$ hydrocarbons" is meant to describe all hydrocarbon molecules having n or more carbon atoms. Accordingly, the term "C$_{5+}$ hydrocarbons" is meant to describe a mixture of hydrocarbons having 5 or more carbon atoms.

Hydrocracking Feed Stream

The hydrocracking feed stream used in the process of the present invention is a mixture comprising C$_5$-C$_{12}$ hydrocarbons, preferably having a boiling point in the range of 30-195° C. Preferably, the hydrocracking feed stream mainly comprises C$_6$-C$_8$ hydrocarbons.

The hydrocracking feed stream may be provided by providing a fresh feed stream and optionally mixing it with another stream, such as a stream recycled from the hydrocracking product stream, such as toluene if desired. This mixing with another stream is optional. If mixing with e.g. a recycle stream does not take place, the hydrocracking feed stream is the same as the fresh feed stream. Suitable examples of fresh feed streams include, but are not limited to first stage or multi-stage hydro-treated pyrolysis gasoline, straight run naphtha, hydrocracked gasoline, light coker naphtha and coke oven light oil, FCC gasoline, reformate or mixtures thereof, which have optionally been subjected to treatments such as hydrogenation, enrichment of mono-aromatic compounds and/or depentanization.

For instance, a typical composition of first stage hydro-treated pyrolysis gasoline may comprise 10-15 wt % $C_5$ olefins, 2-4 wt % $C_5$ paraffins and cycloparaffins, 3-6 wt % $C_6$ olefins, 1-3 wt % $C_6$ paraffins and naphthenes, 25-30 wt % benzene, 15-20 wt % toluene, 2-5 wt % ethylbenzene, 3-6 wt % xylenes, 1-3 wt % trimethylbenzenes, 4-8 wt % dicyclopentadiene, and 10-15 wt % $C_{9+}$ aromatics, alkyl-styrenes and indenes; see e.g. Table E3.1 from Applied Heterogeneous Catalysis: Design, Manufacture, and Use of Solid Catalysts (1987) J. F. Le Page.

It is preferred that the non-aromatic species comprised in the hydrocracking feed stream are saturated (e.g. by the prior hydrogenation) in order to reduce the exotherm within the catalyst bed containing the hydrocracking catalyst used in the present process. Accordingly, preferably, the fresh feed stream is a stream which has been hydrogenated. The hydrogenation advantageously has a further function of hydrodesulphurization. This is advantageous in that the resulting fresh feed stream has a low sulphur content. The low sulphur content in the fresh feed stream is advantageous in that the hydrocracking catalyst used according to the invention does not need to have a hydrodesulphurization function.

The fresh feed stream or the hydrocracking feed stream used in the process may comprise up to 300 parts per million by weight of sulphur (i.e. the weight of sulphur atoms, present in any compound, in relation to the total weight of the feed). For example, the hydrocracking feed stream can comprise sulphur, e.g., greater than zero up to 300, or 5 to 100 parts per million by weight, or 10 to 75 parts per million by weight. The hydrocracking feed stream can be free of sulphur.

In some embodiments, the fresh feed stream used in the process of the present invention is a stream which has been treated to be enriched in mono-aromatic compounds. As used herein, the term "mono-aromatic compound" relates to a hydrocarbon compound having only one aromatic ring. Means and methods suitable to enrich the content of mono-aromatic compounds in a mixed hydrocarbon stream include, for example, the Maxene process; see Bhirud (2002) Proceedings of the DGMK-conference 115-122.

In some embodiments, the fresh feed stream used in the process of the present invention has been depentanized. Preferably, the fresh feed stream comprises at most 5 wt % of $C_5$ hydrocarbons, more preferably at most 4 wt %, at most 3 wt %, at most 2 wt %, at most 1 wt %, or $C_5$ hydrocarbons.

Preferably, the hydrocracking feed stream is provided by a process which does not involve the step of removing benzene or removing $C_6$ hydrocarbons. This means that intentional removal of benzene has not been performed in providing the hydrocracking feed stream or the fresh feed stream. The step of removing benzene typically induces the removal of coboilers of benzene. According to the present invention, the benzene coboilers present in the hydrocracking feed stream are advantageously converted to useful LPG.

Preferably, the hydrocracking feed stream may comprise at least 10 wt % of benzene, for example at least 20 wt % of benzene, at least 30 wt % of benzene or at least 40 wt % of benzene, and/or at most 90 wt % of benzene, for example at most 80 wt %, at most 70 wt %, at most 60 wt % or at most 50 wt % of benzene.

Preferably, the fresh feed stream may comprise at least 10 wt % of benzene, for example at least 20 wt % of benzene, at least 30 wt % of benzene or at least 40 wt % of benzene, and/or at most 90 wt % of benzene, for example at most 80 wt %, at most 70 wt %, at most 60 wt % or at most 50 wt % of benzene.

Step (b)

According to step (b) of the process according to the invention, the hydrocracking feed stream is contacted in the presence of hydrogen in a hydrocracking reactor with the hydrocracking catalyst of the invention.

The product produced by the hydrocracking step of the process of the present invention (hydrocracking product stream) comprises LPG, BTX and methane.

The term "LPG" as used herein refers to the well-established acronym for the term "liquefied petroleum gas". LPG generally consists of a blend of $C_2$-$C_4$ hydrocarbons i.e. a mixture of $C_2$, $C_3$, and $C_4$ hydrocarbons.

The term "BTX" as used herein is well known in the art and relates to a mixture of benzene, toluene and xylenes.

As used herein, the term "chemical grade BTX" relates to a hydrocarbon mixture comprising less than 5 wt % hydrocarbons other than benzene, toluene and xylenes, preferably less than 4 wt % hydrocarbons other than benzene, toluene and xylenes, more preferably less than 3 wt % hydrocarbons other than benzene, toluene and xylenes, and most preferably less than 2.5 wt % hydrocarbons other than benzene, toluene and xylenes.

Furthermore, the "chemical grade BTX" produced by the process of the present invention comprises less than 1 wt % non-aromatic $C_{6+}$ hydrocarbons, preferably less than 0.7 wt % non-aromatic $C_{6+}$ hydrocarbons, more preferably less than 0.5 wt % non-aromatic $C_{6+}$ hydrocarbons and most preferably less than 0.2 wt % non-aromatic $C_{6+}$ hydrocarbons. The most critical contaminants are the non-aromatic species which have boiling points close to benzene including, but not limited to, cyclohexane, methylcyclopentane, n-hexane, 2-methylpentane and 3-methylpentane.

Accordingly, the hydrocracking product stream is substantially free from non-aromatic $C_{6+}$ hydrocarbons. As meant herein, the term "hydrocracking product stream substantially free from non-aromatic $C_{6+}$ hydrocarbons" means that said hydrocracking product stream comprises less than 1 wt % non-aromatic $C_{6+}$ hydrocarbons, preferably less than 0.7 wt % non-aromatic $C_{6+}$ hydrocarbons, more preferably less than 0.5 wt % non-aromatic $C_{6+}$ hydrocarbons and most preferably less than 0.2 wt % non-aromatic $C_{6+}$ hydrocarbons.

The term "aromatic hydrocarbon" is very well known in the art. Accordingly, the term "aromatic hydrocarbon" relates to cyclically conjugated hydrocarbon with a stability (due to delocalization) that is significantly greater than that of a hypothetical localized structure (e.g. Kekulé structure). The most common method for determining aromaticity of a given hydrocarbon is the observation of diatropicity in the 1H NMR spectrum, for example the presence of chemical shifts in the range of from 7.2 to 7.3 ppm for benzene ring protons.

The hydrocracking product stream produced in the process of the present invention preferably comprises less than 5 wt % of methane. Preferably, the hydrocracking product stream produced in the process of the present invention comprises less than 4 wt % of methane, more preferably less than 3 wt % methane, even more preferably less than 2 wt % methane, even more preferably less than 1.5 wt % methane, even more preferably less than 1.4 wt % methane, even more preferably less than 1.3 wt % methane, even more preferably less than 1.2 wt % methane, even more preferably less than 1.1 wt % methane, and most preferably less than 1 wt % methane.

Preferably, the hydrocracking product stream is also substantially free from $C_5$ hydrocarbons. As meant herein, the term "hydrocracking product stream substantially free from $C_5$ hydrocarbons" means that said hydrocracking product stream comprises less than 1 wt % $C_5$ hydrocarbons, preferably less than 0.7 wt % $C_5$ hydrocarbons, more preferably less than 0.6 wt % $C_5$ hydrocarbons and most preferably less than 0.5 wt % $C_5$ hydrocarbons, based upon a total weight of the hydrocracking product stream.

It is a particular advantage of the method of the present invention that the hydrocracking product stream is substantially free from non-aromatic $C_{6+}$ hydrocarbons as these hydrocarbons usually have boiling points close to the boiling point of $C_{6+}$ aromatic hydrocarbons. Hence, it can be difficult to separate the non-aromatic $C_{6+}$ hydrocarbons from the aromatic $C_{6+}$ hydrocarbons comprised in the hydrocracking product stream by distillation. As meant herein, the term "hydrocracking product stream substantially free from non-aromatic $C_{6+}$ hydrocarbons" means that said hydrocracking product stream comprises less than 0.7 wt % non-aromatic $C_{6+}$ hydrocarbons, preferably less than 0.5 wt % non-aromatic $C_{6+}$ hydrocarbons, more preferably less than or equal to 0.2 wt % non-aromatic $C_{6+}$ hydrocarbons and most preferably less than or equal to 0.1 wt % non-aromatic $C_{6+}$ hydrocarbons, based upon a total weight of the hydrocracking product stream.

Process Conditions

The process conditions under which the hydrocracking of the feed stream is performed are an important determinant for the composition of the hydrocracking product stream.

In general, when the space velocity is too high, not all co-boilers of BTX are hydrocracked, so it will not be possible to obtain a chemical grade BTX by simple distillation of the product stream. However, at too low space velocity the yield of methane rises at the expense of propane and butane. Also, a higher space velocity requires smaller reactor volumes and thus a lower CAPEX. Hence, it is advantageous to perform the process of the invention at a high space velocity at which substantially all co-boilers of BTX are hydrocracked.

It was found that the hydrocracking step (b) can advantageously be performed at a high space velocity while allowing substantially all co-boilers of BTX to be hydrocracked, due to the high activity of the catalyst. In the catalyst used in the process of the invention, without wishing to be bound by theory, the hydrogenating metal and the zeolite acid site are in close proximity to one another which translates into a shorter diffusion length between the two sites. This allows BTX co-boilers to be hydrocracked at a high space velocity.

Accordingly, in some preferred embodiments, the step (b) is performed at a Weight Hourly Space Velocity (WHSV) of 0.1-30 hr$^{-1}$, for example at least 1 hr$^{-1}$, at least 2 hr$^{-1}$, at least 3 hr$^{-1}$, at least 5 hr$^{-1}$, at least 6 hr$^{-1}$, at least 7 hr$^{-1}$, or at least 8 hr$^{-1}$, and/or at most 25 hr$^{-1}$, at most 20 hr$^{-1}$, at most 15 hr$^{-1}$, at most 10 hr$^{-1}$ or at most 9 hr$^{-1}$. High WHSV such as at least 8 hr$^{-1}$ allows particularly small reactor volumes and lower capital expenditure (CAPEX).

It has also been found that step (b) can be operated at a relatively low temperature. This allows for greater operational flexibility as well as lower heat duty and may allow longer cycle lengths. Accordingly, in some preferred embodiments, the step (b) is performed at a temperature of 425-445° C. In other embodiments, the step (b) is performed at a temperature of 450-580° C. The higher temperature range results in a high hydrocracking conversion rate.

The hydrocracking of the feed stream is performed at a pressure of 300-5000 kPa gauge, more preferably at a pressure of 600-3000 kPa gauge, particularly preferably at a pressure of 1000-2000 kPa gauge and most preferably at a pressure of 1200-1600 kPa gauge. By increasing reactor pressure, conversion of $C_{5+}$ non-aromatics can be increased, but higher pressure also increases the yield of methane and the hydrogenation of aromatic rings to cyclohexane species which can be cracked to LPG species. This results in a reduction in aromatic yield as the pressure is increased and, as some cyclohexane and its isomer methylcyclopentane, are not fully hydrocracked, there is an optimum in the purity of the resultant benzene at a pressure of 1200-1600 kPa.

The hydrocracking step is performed in the presence of an excess of hydrogen in the reaction mixture. This means that a more than stoichiometric amount of hydrogen is present in the reaction mixture that is subjected to hydrocracking. Preferably, the molar ratio of hydrogen to hydrocarbon species ($H_2$/HC molar ratio) in the reactor feed is between 1:1 and 4:1, preferably between 1:1 and 3:1 and most preferably between 2:1 and 3:1. A higher benzene purity in the product stream can be obtained by selecting a relatively low $H_2$/HC molar ratio. In this context the term "hydrocarbon species" means all hydrocarbon molecules present in the reactor feed such as benzene, toluene, hexane, cyclohexane, etc. It is necessary to know the composition of the feed to then calculate the average molecular weight of this stream to be able to calculate the correct hydrogen feed rate. The excess amount of hydrogen in the reaction mixture suppresses the coke formation which is believed to lead to catalyst deactivation.

Step (c)

The hydrocracking product stream comprises methane, LPG, BTX. The hydrocracking product stream may be subjected to separation by standard means and methods suitable for separating methane and unreacted hydrogen comprised in the hydrocracking product stream as a first separate stream, the LPG comprised in the hydrocracking product stream as a second separate stream and BTX as a third separate stream. Preferably, the stream comprising BTX is separated from the hydrocracking product stream by gas-liquid separation or distillation.

One non-limiting example of such a separation method of the hydrocracking product stream includes a series of distillation steps. The first distillation step at moderate temperature is to separate most of the aromatic species (liquid product) from the hydrogen, $H_2S$, methane and LPG species. The gaseous stream from this distillation is further cooled (to about −30° C.) and distilled again to separate the remaining aromatics species and most of the propane and butane. The gaseous product (mainly hydrogen, $H_2S$, methane and ethane) is then further cooled (to about −100° C.) to separate the ethane and leave the hydrogen, $H_2S$ and methane in the gaseous stream that will be recycled back to the hydrocracking reactor. To control the levels of $H_2S$ and methane in the reactor feed, a proportion of this recycle gas stream is removed from the system as a purge. The quantity of material that is purged depends on the levels of methane and $H_2S$ in the recycle stream which in turn depend on the feed composition. As the purge will contain mainly hydrogen and methane it is suitable for use as a fuel gas or may be further treated (e.g. via a pressure swing adsorption unit) to separately recover a high purity hydrogen stream and a methane/$H_2S$ stream which can be used as a fuel gas.

In a further embodiment, the present invention relates to a process for producing benzene from a feed stream comprising $C_5$-$C_{12}$ hydrocarbons, wherein the said process comprises the process for hydrocracking a feed stream of the present invention further comprising the step of contacting the BTX (or only the toluene and xylenes fraction of said BTX produced) with hydrogen under conditions suitable to produce a hydrodealkylation product stream comprising benzene and fuel gas.

The conditions suitable to produce a hydrodealkylation product stream comprising benzene and fuel gas are well-known and are described in detail e.g. in WO2013/182534, incorporated herein by reference.

Processes for hydrodealkylation of hydrocarbon mixtures comprising $C_6$-$C_9$ aromatic hydrocarbons include thermal hydrodealkylation and catalytic hydrodealkylation; see e.g. WO 2010/102712 A2. Catalytic hydrodealkylation is preferred in the context of the present invention as this hydrodealkylation process generally has a higher selectivity towards benzene than thermal hydrodealkylation. Preferably catalytic hydrodealkylation is employed, wherein the hydrodealkylation catalyst is selected from the group consisting of supported chromium oxide catalyst, supported molybdenum oxide catalyst, platinum on silica or alumina and platinum oxide on silica or alumina.

The process conditions useful for hydrodealkylation, also described herein as "hydrodealkylation conditions", can be easily determined by the person skilled in the art. The process conditions used for thermal hydrodealkylation are for instance described in DE 1668719 A1 and include a temperature of 600-800° C., a pressure of 3-10 MPa gauge and a reaction time of 15-45 seconds. The process conditions used for the preferred catalytic hydrodealkylation preferably include a temperature of 500-650° C., a pressure of 3.5-7 MPa gauge and a Weight Hourly Space Velocity of 0.5-2 $hr^{-1}$; see also Handbook of Commercial Catalysts: Heterogeneous Catalysts ed. Howard F. Rase (2000) Loc. cit.

The hydrodealkylation product stream is typically separated into a liquid stream (containing benzene and other aromatics species) and a gas stream (containing hydrogen, $H_2S$, methane and other low boiling point hydrocarbons) by a combination of cooling and distillation. The liquid stream may be further separated, by distillation, into a benzene stream, a $C_7$ to $C_9$ aromatics stream and a heavy aromatic stream. The $C_7$ to $C_9$ aromatic stream, or some part of it, may be fed back to reactor section as a recycle to increase overall conversion and benzene yield. The heavy aromatic stream, which contains polyaromatic species such as biphenyl, is preferably not recycled to the reactor but may be exported as a separate product stream. The gas stream contains significant quantities of hydrogen and may be recycled back, via a recycle gas compressor, to the reactor section. A recycle gas purge may be used to control the concentrations of methane and $H_2S$ in the reactor feed.

It is noted that the invention relates to all possible combinations of features described herein, and preferred in particular are those combinations of features that are present in the claims. It will therefore be appreciated that all combinations of features relating to the composition according to the invention, all combinations of features relating to the process according to the invention, and all combinations of features relating to the composition according to the invention and features relating to the process according to the invention are described herein.

It is further noted that the term 'comprising' does not exclude the presence of other elements. However, it is also to be understood that a description of a product/composition comprising certain components also discloses a product/composition consisting of these components. The product/composition consisting of these components may be advantageous in that it offers a simpler, more economical process for the preparation of the product/composition. Similarly, it is also to be understood that a description of a process comprising certain steps also discloses a process consisting of these steps. The process consisting of these steps may be advantageous in that it offers a simpler, more economical process.

EXAMPLES

The invention is now elucidated by way of the following examples, without however being limited thereto.

Materials Used for Catalyst Synthesis:
1. Alumina powder (HiQ alumina, # Q-1665 obtained from Alcoa; or Catapal D alumina obtained from Zeolyst)
2. ZSM-5 zeolite powder (CBV 5524G, Zeolyst International). The ZSM-5 was in $NH_4$-form having silica to alumina ratio of 56-58. Unless stated otherwise the zeolite powder was used "as-obtained" from the source without further treatment. The zeolite powder contained less than 0.04 wt % Na. The as-obtained ZSM-5 zeolite powder was calcined at 550° C. for 10 hours (hr) in air prior to use for making Catalyst A-E
3. $HNO_3$ (Sigma-Aldrich, 70%, lot #70296CK)
4. Chloroplatinic acid, $H_2PtCl_6.6H_2O$ (Sigma-Aldrich, lot # MKBR5059V)
5. Tetraamine platinum nitrate, $(NH_3)_4Pt(NO_3)_2$ (Aldrich, LOT # MKBJ1197V)
6. ZSM-5 extrudates (CBV 5524G CY1.6, Zeolyst International). The as-obtained extrudates contained about 80 w % ZSM-5 (silica to alumina ratio 56-58) and 20 wt % alumina binder; the as-obtained zeolite extrudates were calcined and the zeolite present in the extrudates were in H-form. The zeolite contained less than 0.04 wt % Na.
7. Water used is deionized water.

Example Catalysts

Catalyst A 10 grams (g) of alumina powder (HiQ) was treated with 1.6 g of $HNO_3$ by adding slowly while mixing them in a ceramic dish.

A chloroplatinic acid solution was made by dissolving 0.1062 g of $H_2PtCl_6.6H_2O$ in 8 g water. The chloroplatinic acid solution was thereafter added (drop wise) to 40 g of the precalcined ZSM-5 powder and they were mixed well.

As described above the treated zeolite and alumina were combined together, mixed well and then water (22.5 g) was added to make a paste. Paste was formed into shape of beads. Beads were dried at 90° C. for 3 hours, then calcination was continued at temperature ramp 3° C./min up to 300° C. and was kept for 2 hours.

Catalyst B 10 g of alumina powder (HiQ) was treated with 1.6 g of $HNO_3$ by adding slowly while mixing them in a ceramic dish.

A solution of tetraammineplatinum nitrate was made by dissolving 0.0796 g of $(NH_3)_4Pt(NO_3)_2$ in 8 g of water, and the Pt-solution was added (drop wise) to 40 g of ZSM-5 powder (precalcined) mixing them well.

The treated zeolite and alumina were combined together, mixed well and then water (25 g) was added to make a paste. Paste was formed into shape of beads. Beads were dried at 90° C. for 3 hours, then calcination was continued at temperature ramp 3° C./min up to 300° C. and was kept for 2 hours.

Catalyst C 10 g of alumina powder (HiQ) was treated with 1.6 g of $HNO_3$ by adding slowly while mixing them in a ceramic dish. A solution of 0.1072 g of $H_2PtCl_6.6H_2O$ in 2 g of water was added (drop wise) to the alumina while mixing. White color of alumina changed to yellowish.

40 g of ZSM-5 powder (precalcined) was combined with the alumina, mixed well and about 37-38 g of water was added to make a paste. The paste was formed into shape of beads. Beads were dried at 90° C. overnight, then calcination was continued at temperature ramp 3° C./min at 300° C. and was kept for 2 hours.

Catalyst D 10 g of alumina powder (HiQ) was treated with 1.6 g of $HNO_3$ by adding slowly while mixing them in a ceramic dish.

40 g of ZSM-5 powder (precalcined) was combined with the alumina and mixed well. About 25 g of water was added to the zeolite and alumina mixture to moisten. Solution of 0.1062 g of $H_2PtCl_6.6H_2O$ in 15 g of water was prepared and was added to the mixture by portions with careful mixing and finally paste formation. The paste was formed in shape of beads. Beads were dried at 90° C. overnight, then calcination was continued at temperature ramp 3° C./min at 300° C. for 2 hours.

Catalyst E 10 g of alumina powder (HiQ) was treated with 1.6 g of $HNO_3$ by adding the acid slowly to the alumina while mixing them in a ceramic dish.

A Pt-solution was made of 0.3717 g of $H_2PtCl_6.6H_2O$ in 8 g of water. 40 g of ZSM-5 powder (precalcined) was impregnated with the Pt-solution by drops with constant mixing. The zeolite was combined with the alumina and mixed them well. The zeolite and alumina mixture was made into a paste by slowly adding and mixing of about 22.5 g of water. Paste was formed in shape of 1/16-inch cylindrical extrudates. The extruded catalyst was dried/calcined by using a temperature profile: room temperature to 90° C. with ramp 5° C./min (held 3 hr), ramp 3° C./min to 300° C. (held 2 hr).

Catalyst F 20 g of alumina powder (Catapal D) was treated with 3.2 g of $HNO_3$ by adding the acid slowly to the alumina while mixing them in a ceramic dish.

80 g of ZSM-5 zeolite powder was mixed with 38.58 g of 0.005 M solution of $H_2PtCl_6$. The zeolite powder was then combined with the acid treated alumina and mixed well, and an additional 16.26 g water added to the zeolite-alumina mixture to form an extruadable paste.

The paste was extruded as 1/16-inch cylindrical shaped extrudate. The extrudates were dried/calcined in air at 319° C. for 2 hr.

Catalyst G 50 g of alumina powder (Catapal D) was treated with 8.0 g of $HNO_3$ by adding the acid slowly to the alumina while mixing them in a ceramic dish.

A Pt-solution was made of 0.2657 g of $H_2PtCl_6.6H_2O$ in 21 g of water. 50 g of ZSM-5 powder was impregnated with the Pt-solution by drops with constant mixing. The zeolite powder was then combined with the acid treated alumina and mixed well, and an additional 37.24 g water added to the zeolite-alumina mixture to form an extruadable paste.

The paste was extruded as 1/16-inch cylindrical shaped extrudate. The extrudates were dried/calcined in air at 319° C. for 2 hr.

Comparative Catalyst H 8.2017 g of 0.005M $(NH_3)_4Pt(NO_3)_2$ solution were diluted in 49.2 g water in a 500 milliliter (ml) conical glass flask.

10 g of extrudates (which were predried at 300° C. for 5 h) were poured into solution. The mixture was stirred at 60° C. for 24 hours. Then solution was decanted and sample was rinsed with 500 ml water 5 times and then stirred in 300 ml of water for 10 min. Then water was decanted and sample was dried at 90° C. overnight and calcined at 280° C. for 6 hours at temperature ramp 3° C./min.

Comparative Catalyst I 82.148 g of 0.005M $H_2PtCl_6.6H_2O$ solution were diluted in 204.97 g water in a 3.5 L glass beaker.

100 g of extrudates (which were predried at 150° C. overnight) were poured into solution. The mixture was stirred at 60° C. for 24 hours. Then solution was decanted and sample was rinsed with 1 liter (L) water 5 times and then stirred in 1 L of water for 10 min. Then water was decanted and sample was dried at 90° C. overnight and calcined at 280° C. for 6 hours at temperature ramp 3° C./min.

Comparative Catalyst J 10 g of extrudates were stirred in 28.678 g of 0.005M $H_2PtCl_6.6H_2O$ solution at 60° C. for 24 hours. Then solution was decanted and sample was rinsed several times with water and stirred in 500 ml of water for 25 min. Then water was decanted and sample was dried at 90° C. overnight and calcined at 280° C. for 3 hours at temperature ramp 3° C./min.

The catalyst preparation methods with Pt content are summarized in Table 1.

TABLE 1

| Catalyst | Pt deposition[1] | Pt source | Pt, wt % |
|---|---|---|---|
| A | Zeolite powder | $H_2PtCl_6$ | 0.060 |
| B | Zeolite powder | $(NH_3)_4Pt(NO_3)_2$ | 0.065 |
| C | Alumina powder | $H_2PtCl_6$ | 0.067 |
| D | Zeolite-alumina powder | $H_2PtCl_6$ | 0.072 |
| E | Zeolite powder | $H_2PtCl_6$ | 0.256 |
| F | Zeolite powder | $H_2PtCl_6$ | 0.070 |
| G | Zeolite powder | $H_2PtCl_6$ | 0.070 |
| H | Extrudate | $(NH_3)_4Pt(NO_3)_2$ | 0.07 |
| I | Extrudate | $H_2PtCl_6$ | 0.07 |
| J | Extrudate | $H_2PtCl_6$ | 0.25 |

[1]Pt was added either to zeolite or alumina during forming or deposited on formed extrudates Catalyst Testing:

The catalysts A-J were tested for hydrocracking reaction using stainless steel tube reactor as described below. 0.10 g catalyst (sized 20-40 mesh) was diluted to 3 ml by premixing with SiC (30 grit) and was loaded in a reactor.

Reactor description: one quarter inch (1/4") tube, 0.028" wall thickness. 1/16" thermocouple with a 1/8" spacer bar; 12"×1" brass over-sleeve; reactor bed is approx. 5-6 inches (") in length in center of sleeve.

The catalyst was pre-activated (drying, Pt reduction) by subjecting it to 40 standard cubic centimeters (sccm) of $H_2$ per minute at 130° C. under 50 psig for 2 hours and subsequently 40 sccm of $H_2$ (with 50 ppm of $H_2S$) at 350° C. at 50 psig for 30 min.

The hydrocracking feed stream consisted of 70 wt % benzene, 15 wt % 3-methylpentane and 15 wt % methylcyclopentane. All components of the hydrocracking feed stream are Aldrich reagent grade chemicals dried under 4 A molecular sieves overnight.

The hydrocracking feed stream was introduced to the reactor at a temperature of 470° C. and a pressure of 200 psig. The liquid feed rate was adjusted to give WHSV of about 10/hr. The molar ratio of $H_2$ to the hydrocarbons was 4 to 1, and the $H_2S$ content was 50 parts per million by mole (ppm) based on the total hydrocarbon and $H_2$ feed.

To illustrate the invention Example Catalysts A-G were used in Experiments 1-7 whereas Comparative Catalysts H-J were used in Experiments 8-10. In all experiments the catalysts were tested under the same conditions as described in preceding paragraphs. The catalytic activity was measured by comparing benzene purity which was calculated by following formula:

% benzene purity=% benzene/(% benzene+% $C_6$-nonaromatic hydrocarbons)

where % is as C % in product stream.

The catalyst activity is shown in Table 2 and illustrated in FIG. 1. The selectivity was calculated as % C basis. The catalyst activity and selectivity were averaged from data over a period of about 20 hours after the catalyst reached to steady-state conditions.

TABLE 2

Catalyst activity and selectivity

| Example | Catalyst | WHSV/hr | Activity (benzene purity) | Selectivity (% C) | | | |
|---|---|---|---|---|---|---|---|
| | | | | Methane | LPG | Benzene | Total Aromatics |
| 1 | A | 10.01 | 99.90 | 1.37 | 29.72 | 63.48 | 67.91 |
| 2 | B | 10.01 | 99.88 | 1.32 | 30.74 | 62.43 | 67.61 |
| 3 | C | 10.01 | 99.86 | 1.28 | 31.51 | 61.24 | 66.87 |
| 4 | D | 10.01 | 99.86 | 1.32 | 31.34 | 61.16 | 67.00 |
| 5 | E | 10.01 | 99.84 | 1.34 | 38.24 | 54.77 | 60.05 |
| 6 | F | 10.01 | 99.88 | 1.35 | 26.45 | 65.74 | 71.90 |
| 7 | G | 10.01 | 99.62 | 1.00 | 31.87 | 61.58 | 66.46 |
| Comp 8 | H | 9.72 | 99.63 | 1.29 | 29.99 | 62.42 | 69.76 |
| Comp 9 | I | 9.91 | 99.80 | 1.20 | 31.97 | 61.81 | 66.39 |
| Comp 10 | J | 9.91 | 99.71 | 1.30 | 44.03 | 48.71 | 53.52 |

Under these conditions, all catalysts were shown to crack the 3-methylpentane and methylcyclopentane.

The catalysts according to the invention show an improved or at least the same hydrocracking activity giving the same or increased benzene purity as shown in table above.

Calcination Temperature Analysis

The effect of calcination temperature on the platinum (Pt) particle size was examined. The calcination was in air at the temperature set forth in Table 3. The particle size was determined using a Scanning Transmission Electron Microscopy (STEM) using a TECNAI-F20 microscope, measuring at least 6 particles. High Angular Annular Dark Field (HAADF) detector was used in the STEM mode to study the material.

As can be seen in Table 3, as the calcination temperature increases, the particle size increases. The change from 500° C. to 600° C. increased the particle size by nearly 300%. Changing the calcination temperature from 280° C. to 500° C. showed an increase of well over 500%. Actually, Table 3 shows that the average Pt particle size is less than or equal to 1 nm when the Pt containing catalyst was calcined at 280° C. in air, yet well over 10 nm when calcined at higher temperatures such as 500° C. Smaller particle sizes have greater surface area and greater activity. Clearly calcining at a higher temperature produces a different catalyst.

Set forth below are some embodiments of the catalyst, method of making the catalyst, and method of using the catalyst disclosed herein.

Embodiment 1

A process for preparing a hydrocracking catalyst, comprising: (i) combining a zeolite, a binder, water and a hydrogenating metal compound which is a complex or a salt of a hydrogenating metal to obtain a mixture, wherein the zeolite has not been treated by a phosphorus-containing compound and the zeolite has a silica to alumina molar ratio of 5-200; (ii) forming the mixture into a shaped body; and (iii) calcining the shaped body at 250-300° C., preferably 250-295° C., for 2-8 hours to form the catalyst.

Embodiment 2

The process according to any one of the preceding embodiments, wherein the catalyst has an average hydrogenating metal particle size of less than or equal to 5 nm, preferably less than or equal to 3 nm, or less than or equal to 2 nm, as determined using TEM.

TABLE 3

| Example | Catalyst | Calcination 1 time (hr) at 280° C. | Further Calcination time (hr)[2] | Calcination Temperature (° C.) | Pt wt % | Average Pt particle size (nm) |
|---|---|---|---|---|---|---|
| 11 | I | 6 | — | 280 | 0.070 | (not detected)[1] |
| 12 | I | 6 | 3 | 600 | 0.070 | 14.7 |
| 13 | E | 2 | — | 280 | 0.256 | 0.9 |
| 14 | E | 2 | 3 | 500 | 0.256 | 25 |
| 15 | E | 2 | 2 | 600 | 0.256 | 99 |

[1]Below detection limit of 0.5 nm.
[2]The catalyst was initially calcined at 280° C. and then further calcined at the higher temperature to determine the effect of calcining at a higher temperature. The ramp rate was 2° C./min.

Embodiment 3

The process according to any one of the preceding embodiments, wherein the mixture is a paste.

Embodiment 4

A process for preparing a hydrocracking catalyst, comprising: (i) combining a zeolite, a binder, and a hydrogenating metal compound which is a complex or a salt of a hydrogenating metal, with water to form a paste, wherein the zeolite has not been treated by a phosphorus-containing compound, and wherein the zeolite has a silica to alumina molar ratio of 5-200; (ii) forming the paste into a shaped body; and (iii) calcining the shaped body to form the catalyst; wherein the catalyst has an average hydrogenating metal particle size of less than or equal to 5 nm, preferably less than or equal to 3 nm, or less than or equal to 2 nm, as determined using TEM.

Embodiment 5

The process according to Embodiment 4, wherein the shaped body is calcined at 250-300° C., preferably 250-295° C., for 2-8 hours.

Embodiment 6

The process according to any one of Embodiments 3-5, wherein the paste is an extrudable paste.

Embodiment 7

The process according to any of the preceding embodiments, wherein step (i) involves: combining the zeolite and the hydrogenating metal compound and subsequently adding the binder to the combination of the zeolite and the hydrogenating metal compound; or combining the hydrogenating metal compound and the binder and subsequently adding the zeolite to the combination of the binder and the hydrogenating metal compound.

Embodiment 8

The process according to any one of the preceding embodiments, wherein the zeolite is selected from the group consisting of ZSM-5, MCM-22, ZSM-11, beta zeolite, EU-1 zeolite, faujasite (zeolite Y), ferrierite and mordenite and preferably the zeolite is ZSM-5.

Embodiment 9

The process according to any one of the preceding embodiments, wherein the silica to alumina molar ratio is 25-75, preferably 30-65, more preferably 35-60, more preferably 40-55.

Embodiment 10

The process according to any one of the preceding embodiments, wherein the zeolite is an $H^+$-form or $NH_4^+$-form.

Embodiment 11

The process according to any one of the preceding embodiments, wherein the binder is an inorganic oxide material preferably selected from the group consisting of alumina, clay, silica-alumina, aluminum phosphate and combinations thereof, preferably alumina.

Embodiment 12

The process according to any one of the preceding embodiments, wherein the binder has been treated with a mineral acid such as nitric acid, hydrochloric acid, phosphoric acid or sulfuric acid, preferably nitric acid.

Embodiment 13

The process according to any one of the preceding embodiments, wherein the amount of binder is 10 to 90 wt % relative to the total weight of the catalyst.

Embodiment 14

The process according to any one of the preceding embodiments, wherein the hydrogenating metal is at least one element selected from Group 10 of the periodic table of elements or rhodium or iridium, preferably palladium or platinum, most preferably platinum.

Embodiment 15

The process according to any one of the preceding embodiments, wherein the hydrogenating metal compound is selected from the group consisting of $H_2PtCl_6$, $(NH_3)_4Pt(NO_3)_2$, $(NH_3)_4Pt(OH)_2$ and $(NH_3)_4PtCl_2$.

Embodiment 16

The process according to any one of the preceding embodiments, wherein the amount of the hydrogenating metal is 0.010-0.30 wt %, preferably 0.015-0.095 wt %, more preferably 0.035-0.080 wt %, with respect to the total catalyst.

Embodiment 17

The process according to any one of the preceding embodiments, wherein the shaped body is an extrudate having an average diameter of 0.5-5 mm.

Embodiment 18

The process according to any one of the preceding embodiments, wherein the only metal in the catalyst is the hydrogenating metal.

Embodiment 19

The process according to any one of the preceding embodiments, wherein the hydrogenating metal consists of at least one element selected from Group 10 of the periodic table of elements, rhodium, and iridium, preferably the hydrogenating metal consists of at least one of palladium and platinum, most preferably the hydrogenating metal consists of platinum.

Embodiment 20

The process according to any one of the preceding embodiments, wherein the shaped body consists of the zeolite, the binder, the water, and the hydrogenating metal compound.

Embodiment 21

The process according to any one of the preceding embodiments, wherein the catalyst consists of the calcined shaped body.

Embodiment 22

The process according to any one of the preceding embodiments, wherein the shaped body is formed before the hydrogenating metal and binder are calcined.

Embodiment 23

The process according to any one of the preceding embodiments, wherein catalyst comprises platinum, and preferably comprises less than 0.01 wt % of the hydrogenating metals, based upon the total weight of the catalyst.

Embodiment 24

The process according to any one of the preceding embodiments, wherein the mixture is mixed for a period of time of less than or equal to 20 minutes, preferably less than or equal to 10 minutes, prior to forming into the shaped body.

Embodiment 25

The hydrocracking catalyst obtainable by the process according to any one of the preceding embodiments.

Embodiment 26

A process for hydrocracking a feed stream comprising hydrocarbons by contacting the feed stream in the presence of hydrogen with the hydrocracking catalyst according to Embodiment 25.

Embodiment 27

The process according to Embodiment 26, comprising: contacting a hydrocracking feed stream in the presence of hydrogen with a hydrocracking catalyst to produce a hydrocracking product stream comprising BTX, preferably the contacting is under process conditions including a temperature of 400-580° C., a pressure of 300-5000 kPa gauge and a Weight Hourly Space Velocity of 0.1-30 hr$^{-1}$, wherein the hydrocracking feed stream comprises $C_5$-$C_{12}$ hydrocarbons; and (c) separating the BTX from the hydrocracking product stream.

The present application claims priority to EP Application No. 16182324.0 filed on Aug. 2, 2016, which is incorporated herein in its entirety.

The invention claimed is:

1. A process for preparing a hydrocracking catalyst, comprising:
   (i) combining a zeolite, a binder, water and a hydrogenating metal compound which is a complex or a salt of a hydrogenating metal to obtain a mixture, wherein the zeolite has not been treated by a phosphorus-containing compound and the zeolite has a silica to alumina molar ratio of 5-200;
   (ii) forming the mixture into a shaped body; and
   (iii) calcining the shaped body at 250 to less than 300° C., for 2-8 hours to form the catalyst.

2. The process according to claim 1, wherein the catalyst has an average hydrogenating metal particle size of less than or equal to 5 nm, as determined using TEM.

3. The process according to claim 1, wherein the mixture is an extrudable paste.

4. A process for preparing a hydrocracking catalyst, comprising:
   (i) combining a zeolite, a binder, and a hydrogenating metal compound which is a complex or a salt of a hydrogenating metal, with water to form a paste, wherein the zeolite has not been treated by a phosphorus-containing compound;
   (ii) forming the paste into a shaped body; and
   (iii) calcining the shaped body at 250-295° C. to form the catalyst;
   wherein the catalyst has an average hydrogenating metal particle size of less than or equal to 5 nm, as determined using TEM.

5. The process according to claim 1, wherein the shaped body is calcined at 250-295° C.

6. The process according to claim 1, wherein the catalyst comprises less than 0.01 parts tin, less than 0.02 parts lead, and less than 0.01 parts bismuth, on the basis of 100 parts by weight of the catalyst.

7. The process according to claim 1, wherein step (i) involves
   combining the zeolite and the hydrogenating metal compound and subsequently adding the binder to the combination of the zeolite and the hydrogenating metal compound; or
   combining the hydrogenating metal compound and the binder and subsequently adding the zeolite to the combination of the binder and the hydrogenating metal compound.

8. The process according to claim 1, wherein the zeolite is selected from the group consisting of ZSM-5, MCM-22, ZSM-11, beta zeolite, EU-1 zeolite, faujasite (zeolite Y), ferrierite and mordenite.

9. The process according to claim 1, wherein the silica to alumina molar ratio is 25-75.

10. The process according to claim 1, wherein the zeolite is an H$^+$-form or NH$_4^+$-form.

11. The process according to claim 1, wherein the binder is selected from the group consisting of alumina, clay, silica-alumina, aluminum phosphate and combinations thereof.

12. The process according to claim 1, wherein the binder has been treated with a mineral acid.

13. The process according to claim 1, wherein the hydrogenating metal is at least one of palladium and platinum.

14. The process according to claim 1, wherein the hydrogenating metal compound is selected from the group consisting of $H_2PtCl_6$, $(NH_3)_4Pt(NO_3)_2$, $(NH_3)_4Pt(OH)_2$ and $(NH_3)_4PtCl_2$.

15. The process according to claim 1, wherein the amount of the hydrogenating metal is 0.010-0.30 wt %, with respect to the total catalyst.

16. The process according to claim 1, wherein the shaped body is an extrudate having an average diameter of 0.5-5 mm.

17. The process according to claim 1, wherein the hydrogenating metal is at least one element selected from Group 10 of the periodic table of elements, rhodium, and iridium.

18. The process according to claim 1, wherein the shaped body is calcined at 260-290° C.

19. The process according to claim 1, wherein the silica to alumina molar ratio is 20-100.

20. The process according to claim 1, wherein the silica to alumina molar ratio is 25-75.

* * * * *